United States Patent
Hashima

(10) Patent No.: US 10,549,302 B2
(45) Date of Patent: Feb. 4, 2020

(54) OPERATING METHOD OF PROCESSING LIQUID SUPPLY APPARATUS AND RECORDING MEDIUM

(71) Applicant: Tokyo Electron Limited, Tokyo (JP)

(72) Inventor: Hitoshi Hashima, Koshi (JP)

(73) Assignee: TOKYO ELECTRON LIMITED, Tokyo (JP)

(*) Notice: Subject to any disclaimer, the term of this patent is extended or adjusted under 35 U.S.C. 154(b) by 0 days.

(21) Appl. No.: 15/912,652

(22) Filed: Mar. 6, 2018

(65) Prior Publication Data
US 2018/0193862 A1    Jul. 12, 2018

Related U.S. Application Data

(62) Division of application No. 15/275,588, filed on Sep. 26, 2016, now Pat. No. 9,943,871.

(30) Foreign Application Priority Data

Sep. 28, 2015    (JP) ................................. 2015-190097
Sep. 9, 2016    (JP) ................................. 2016-176593

(51) Int. Cl.
| | | |
|---|---|---|
| B05B 12/08 | (2006.01) | |
| B05B 12/02 | (2006.01) | |
| H01L 21/67 | (2006.01) | |
| B05B 12/00 | (2018.01) | |
| G01N 27/00 | (2006.01) | |

(52) U.S. Cl.
CPC .......... *B05B 12/081* (2013.01); *B05B 12/004* (2013.01); *B05B 12/02* (2013.01); *G01N 27/002* (2013.01); *H01L 21/6708* (2013.01); *H01L 21/6715* (2013.01); *H01L 21/67051* (2013.01); *H01L 21/67253* (2013.01)

(58) Field of Classification Search
None
See application file for complete search history.

(56) References Cited

U.S. PATENT DOCUMENTS

| | | | | |
|---|---|---|---|---|
| 2,386,647 A | * | 10/1945 | Andresen ............... | B64D 45/02 204/164 |
| 4,258,736 A | * | 3/1981 | Denbow ................. | G01N 27/06 137/2 |
| 2011/0089137 A1 | | 4/2011 | Tanaka | |

FOREIGN PATENT DOCUMENTS

| | | | |
|---|---|---|---|
| JP | 2006-269677 A | | 10/2006 |
| JP | 2006269677 A | * | 10/2006 |

OTHER PUBLICATIONS

English translation of JP-2006269677-A (Year: 2006).*

* cited by examiner

*Primary Examiner* — Charles D Garber
*Assistant Examiner* — Xiaoming Liu
(74) *Attorney, Agent, or Firm* — Pearne & Gordon LLP

(57) ABSTRACT

An operating method of a processing liquid supply apparatus which supplies a processing liquid to a substrate from a processing liquid supply path via a nozzle includes measuring a surface potential of a first electrode which is configured to be in contact with the processing liquid of the processing liquid supply path. The operating method further includes displaying the measured surface potential in the measuring of the surface potential of the first electrode.

4 Claims, 11 Drawing Sheets

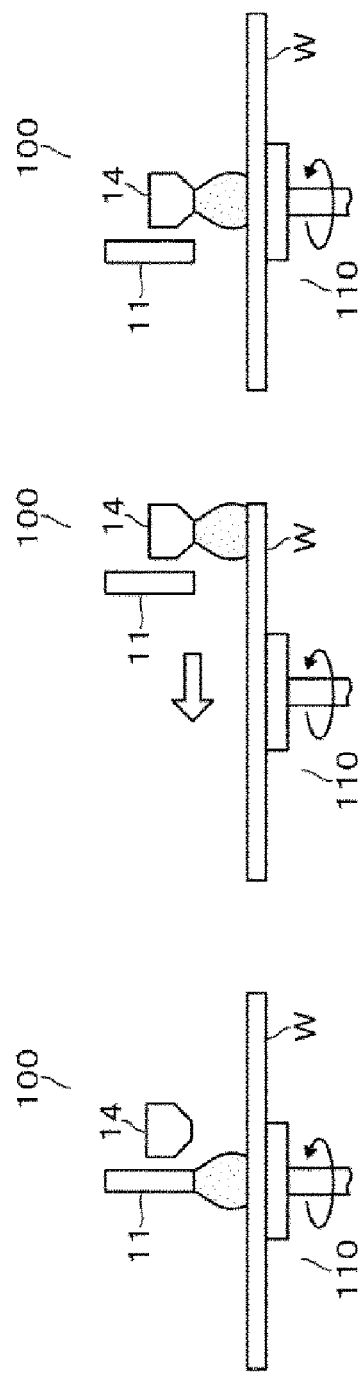

OPERATING METHOD OF PROCESSING LIQUID SUPPLY APPARATUS AND RECORDING MEDIUM

CROSS-REFERENCE TO RELATED APPLICATION

This application is a divisional application of U.S. patent application Ser. No. 15/275,588, filed on Sep. 26, 2016, which claims the benefit of Japanese Patent Application Nos. 2015-190097 and 2016-176593 filed on Sep. 28, 2015 and Sep. 9, 2016, respectively, the entire disclosures of which are incorporated herein by reference.

TECHNICAL FIELD

The embodiments described herein pertain generally to a processing liquid supply apparatus configured to supply a processing liquid onto a substrate from a nozzle, an operating method of the processing liquid supply apparatus, and a recording medium.

BACKGROUND

A single-wafer type liquid processing apparatus employed in a semiconductor manufacturing process is configured to discharge a processing liquid onto a surface of a substrate held on a spin chuck from a nozzle, for example. Examples of liquid processing include a process of coating a resist solution on a substrate to form a resist pattern, a process of supplying a developing solution onto a substrate after exposure, a process of cleaning a substrate by supplying a rinse liquid onto a substrate, and so forth. This processing liquid is supplied into the nozzle through a pipeline which is equipped with such devices as a valve, a filter and a pump.

A flow path including a device or a pipeline is made of an insulating material such as a fluorine resin for the purposes of cleanness or chemical resistance. As known in the art, if a processing liquid is flown into the flow path, static electricity is generated by friction between the flow path and the processing liquid. Depending on the kind of the processing liquid or the processing condition, a charge amount may be increased. As a result, there is a concern that a member forming the flow path is damaged caused by dielectric breakdown thereof or a processing efficiency is deteriorated.

Patent Document 1 describes a method of neutralizing electric charges by grounding the processing liquid via a carbon electrode which is configured to be in contact with the processing liquid. However, there is a concern that the carbon electrode having high purity may be broken or damaged. If an element other than carbon is contained, an impurity may be eluted in the processing liquid, causing contamination of the processing liquid. Further, in the disclosure of Patent Document 1, since the charge amount of the processing liquid cannot be detected, it is difficult to take a response to the charging.

Patent Document 1: Japanese Patent Laid-open Publication No. 2006-269677 (paragraphs [0036] and [0063], FIG. 2, etc.)

SUMMARY

In view of the foregoing, exemplary embodiments provide a technique of detecting a state of a charge amount of a processing liquid by measuring the charge amount as a surface potential when supplying the processing liquid onto a substrate through a processing liquid supply path which is formed by the flow path member having insulating property.

In one exemplary embodiment, a processing liquid supply apparatus which supplies a processing liquid to a substrate from a nozzle includes an insulating flow path member forming a processing liquid supply path through which the processing liquid is supplied to the nozzle; a first electrode configured to be in contact with the processing liquid of the processing liquid supply path; and a surface potential measuring unit configured to measure a surface potential of the first electrode.

In another exemplary embodiment, an operating method of a processing liquid supply apparatus which supplies a processing liquid to a substrate from a processing liquid supply path via a nozzle includes measuring a surface potential of a first electrode which is configured to be in contact with the processing liquid of the processing liquid supply path; and displaying the measured surface potential in the measuring of the surface potential of the first electrode.

In still another exemplary embodiment, there is provided a recording medium having stored thereon computer-executable instructions that, in response to execution, cause a processing liquid supply apparatus to perform an operating method of the processing liquid supply apparatus.

According to the exemplary embodiments as stated above, when supplying the processing liquid to the substrate through the processing liquid supply path formed by the insulating flow path member, the state of the charge amount of the processing liquid is detected as the surface potential of the electrode which is configured to be in contact with the processing liquid of the processing liquid supply path. Accordingly, the charged state of the processing liquid can be detected, which contributes to taking the proper response.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 10A to FIG. 10C are process diagrams illustrating an operation of the processing liquid supply apparatus.

DETAILED DESCRIPTION

Figure 1:
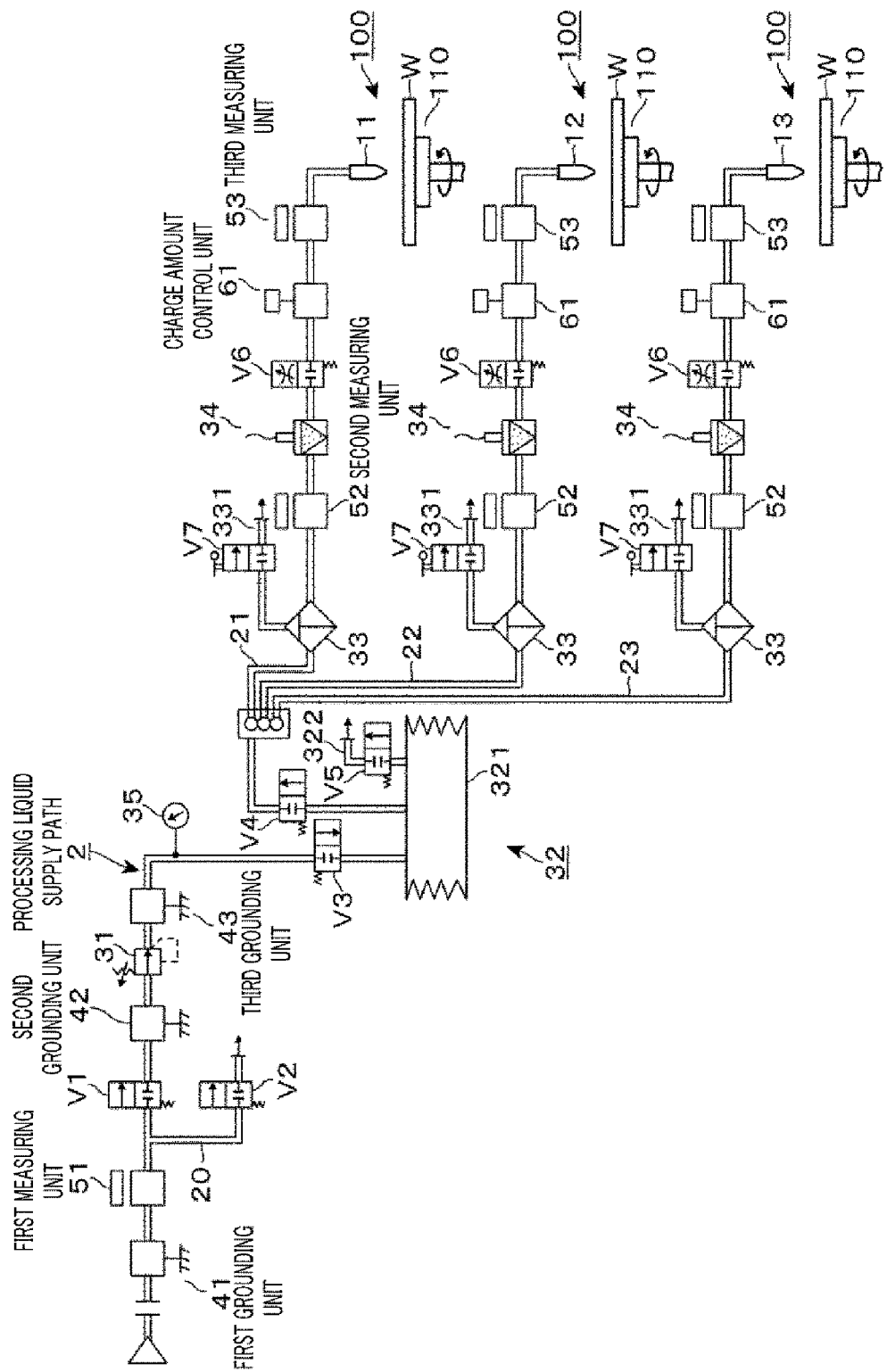
FIG. 1 is a configuration diagram of a processing liquid supply apparatus according to a first exemplary embodiment.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current exemplary embodiment. Still, the exemplary embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

FIG. 1 is diagram illustrating a processing liquid supply apparatus according to a first exemplary embodiment. The processing liquid supply apparatus is configured to supply a processing liquid, e.g., a developing solution, onto a substrate such as a semiconductor wafer (hereinafter, referred to as "wafer") W from nozzles 11, 12 and 13. The processing liquid supply apparatus is equipped with a processing liquid supply path 2 through which the processing liquid is supplied to the nozzles 11, 12 and 13. The processing liquid supply path 2 is formed by an insulating flow path member, and a non-illustrated processing liquid supply source is connected to an upstream end of the processing liquid supply path 2. The flow path member is implemented by, by way of non-limiting example, a pipeline made of a fluorine resin such as PFA (tetrafluoroethylene-perfluoroalkylvinylether copolymer), PTFE (polytetrafluoroethylene), or the like. FIG. 1 illustrates a downstream side of the processing liquid supply source in the processing liquid supply path 2. The processing liquid supply path 2 is equipped with supply devices such as a valve or a pump; and, in the present exemplary embodiment, devices configured to control charge amounts of the processing liquid and the flow path member.

The supply devices such as a valve or a pump will be first explained. The processing liquid supply path 2 is provided with a first valve V1, a regulator 31 and a pump unit 32 in sequence from the upstream side thereof. The first valve V1 is a valve configured to supply the processing liquid into the processing liquid supply apparatus from the processing liquid supply source, and a branch path 20 equipped with a valve V2 for vent is connected to an upstream side of the first valve V1. The regulator 31 is configured to reduce a pressure of the processing liquid which flows in the processing liquid supply path 2 at an upstream side thereof.

The regulator 31 is equipped with, by way of example, a diaphragm and a valve interlocked with the diaphragm, and is configured to adjust a pressure loss by controlling the opening degree of the valve. The pump unit 32 is configured to discharge the processing liquid to the nozzles 11, 12 and 13. This pump unit 32 includes a pump 321 implemented by, e.g., a diaphragm pump; a supply valve V3 for supplying the processing liquid into the pump 321; and a discharge valve V4 for discharging the processing liquid from the pump 321 to the downstream side. Further, the pump 321 is connected to a drain path 322 which is equipped with a drain valve V5.

In the present exemplary embodiment, the processing liquid supply path 2 is branched into three at a downstream side of the discharge valve V4, and each of the three branched processing liquid supply paths will be referred to as a first flow path 21, a second flow path 22 and a third flow path 23, respectively. The nozzle 11, the nozzle 12 and the nozzle 13 are provided at downstream ends of the first flow path 21, the second flow path 22 and the third flow path 23, respectively. These nozzles 11, 12 and 13 are configured to supply the same kind of processing liquid to wafers which are transferred into liquid processing modules 100. Each of the liquid processing modules 100 for developing process is equipped with a substrate holding unit 110 which is configured to hold a wafer W such that the wafer W is pivotable around a vertical axis.

Each of the first flow path 21, the second flow path 22 and the third flow path 23 is provided with a filter 33, a flow detection unit 34 and a dispense valve (liquid discharge valve) V6 in sequence from the upstream side. The dispense valve V6 is a device configured to discharge the processing liquid at a preset liquid amount. The filter 33 is configured to remove a particle contained in the processing liquid, and is provided with a vent path 331 equipped with a vent valve V7. In the present exemplary embodiment, each of the valves V1 to V7 is implemented by, by way of example, but not limitation, an air-operate valve. In FIG. 1, a reference numeral 35 denotes a pressure detection unit.

Before describing the devices regarding the control of the charge amount of the processing liquid which are provided at the processing liquid supply path 2, a charged state of the processing liquid will be first discussed with reference to FIG. 2A to FIG. 4B. The insulating flow path member forming the processing liquid supply path 2 tends to be negatively charged easily, whereas the processing liquid tends to be positively charged easily. Thus, if the processing liquid is flown into the processing liquid supply path 2, static electricity is generated by friction between the flow path member and the processing liquid. A frictional force is increased in a region within the processing liquid supply path 2 where a pressure or a flow velocity is high, so that the charge amount is increased.

Figure 2A:
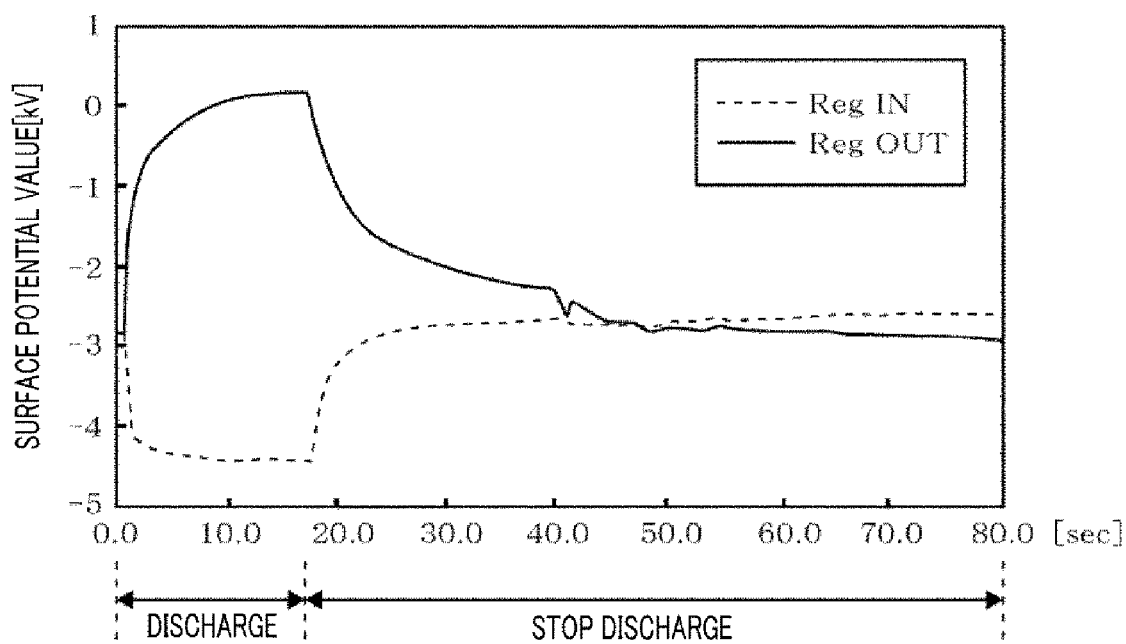
FIG. 2A and FIG. 2B are characteristic diagrams illustrating a relationship between a surface potential value and time.
Figure 2B:
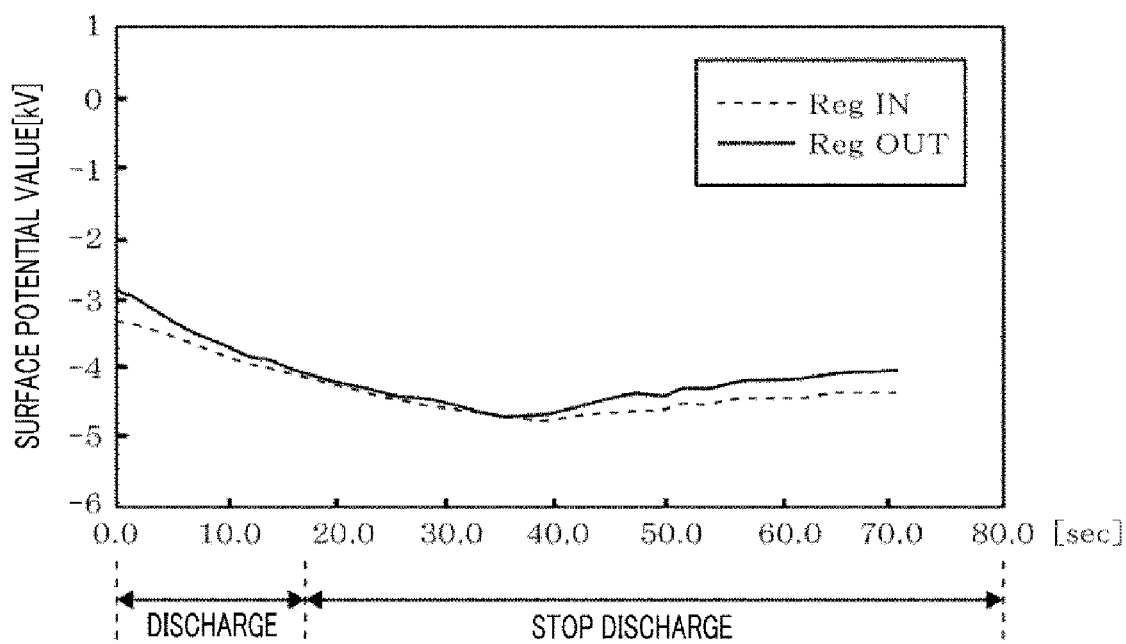

FIG. 2A and FIG. 2B are characteristic diagrams illustrating a relationship between time and a surface potential value at each of a position Reg IN which is closest to the regulator 31 at an upstream side thereof and a position Reg OUT which is closest to the regulator 31 at a downstream side thereof in the processing liquid supply path 2. The surface potential values are acquired by a measuring unit of the surface potential to be described later. FIG. 2A depicts a case where a pressure loss is large, and FIG. 2B illustrates a case where a pressure loss is small. In the drawings, the data of Reg IN and Reg OUT are plotted by a dashed line and a solid line, respectively. As can be seen from FIG. 2A and FIG. 2B, if the processing liquid is discharged from the nozzles 11, 12 and 13, the processing liquid is flown within the processing liquid supply path 2, so that the surface potential of the processing liquid supply path 2 is varied. The variation amount is found to be larger when the pressure loss is large, as compared to the case where the pressure loss is small.

Figure 3A:
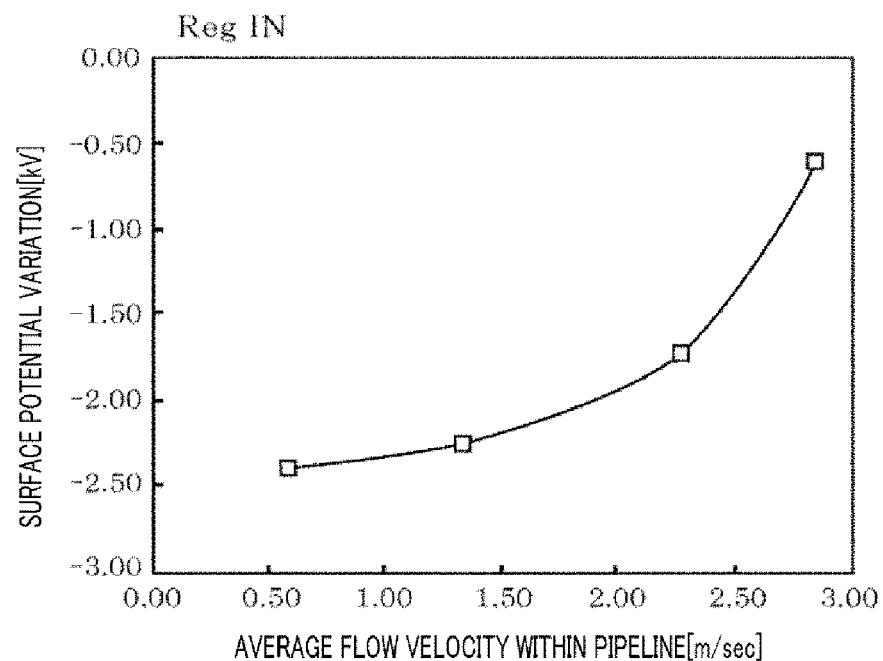
FIG. 3A and FIG. 3B are characteristic diagrams illustrating a relationship between a surface potential variation and a flow velocity.
Figure 3B:
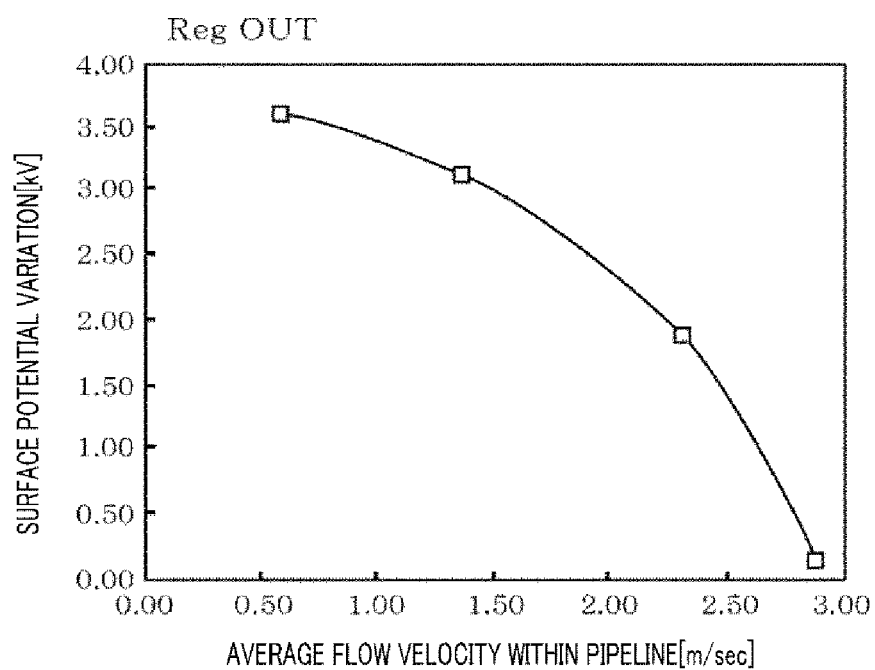

FIG. 3A and FIG. 3B are characteristic diagrams showing a relationship between an average flow velocity within the pipeline and surface potential variations of the processing liquid supply path 2 at the positions Reg IN and Reg OUT, respectively. FIG. 3A depicts the data of Reg IN, and FIG. 3B depicts the data of Reg OUT. The average flow velocity is adjusted by controlling the opening degree of the regulator 31. As the opening degree of the regulator 31 is increased, the flow velocity is increased and the pressure loss is decreased. Here, the surface potential variation means a difference between a measurement value of the surface potential and an initial value of the surface potential (which is measured when no liquid is moving, that is, before the processing liquid is discharged). As can be seen from these data, in case of Reg IN, a minus value of the surface potential variation is increased as the pressure loss is increased, whereas, in case of Reg OUT, a plus value of the surface potential variation is increased as the pressure loss is increased.

Figure 4A:
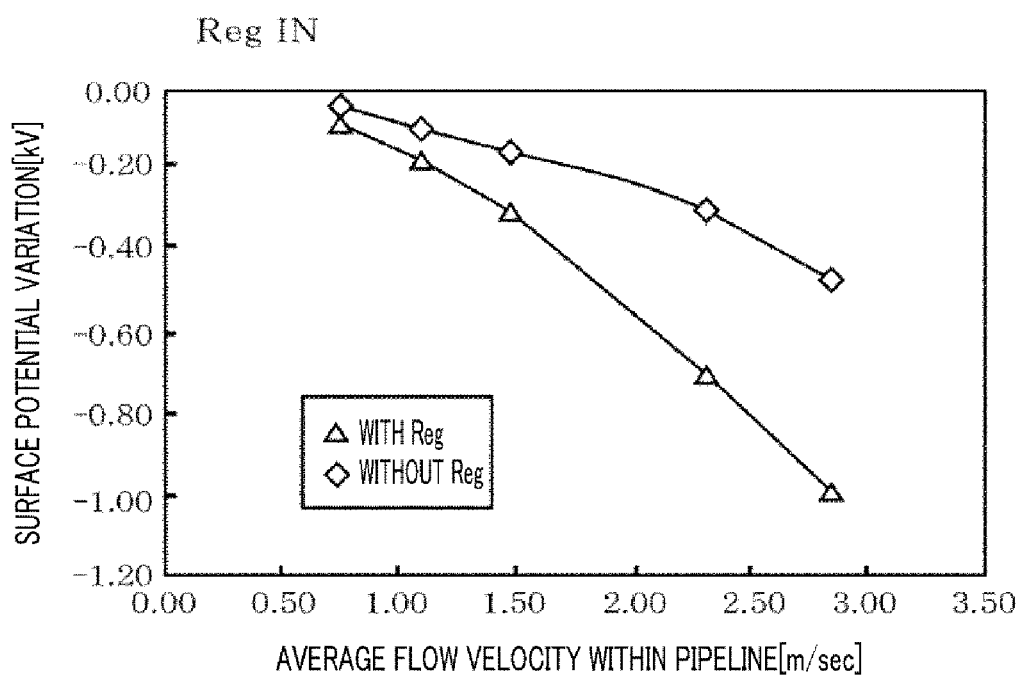
FIG. 4A and FIG. 4B are characteristic diagrams illustrating a relationship between a surface potential variation and a flow velocity.
Figure 4B:
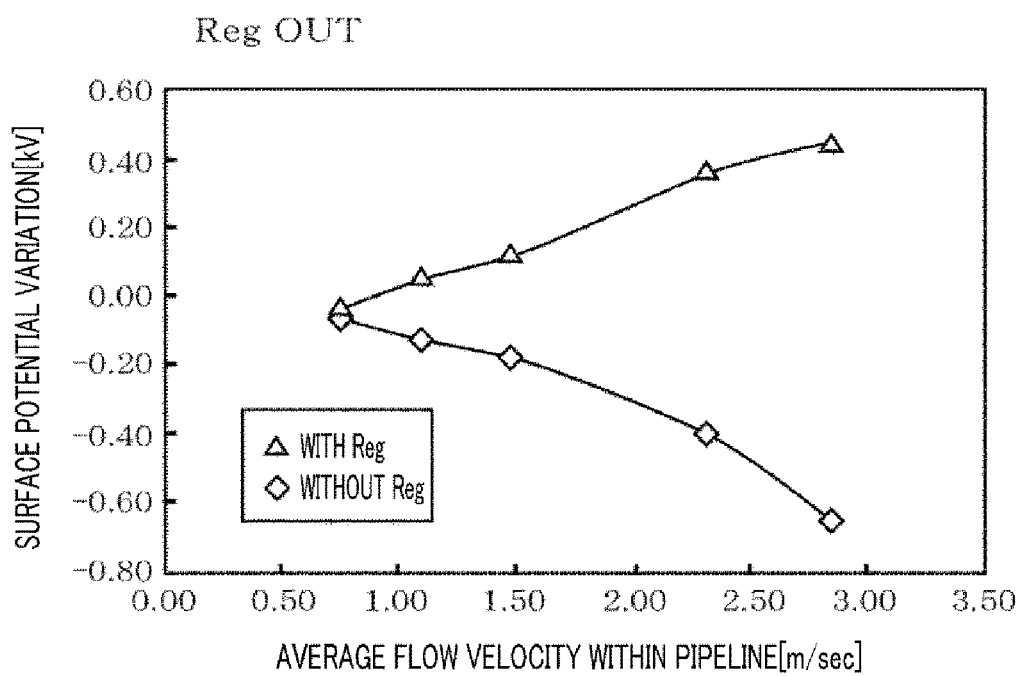

FIG. 4A and FIG. 4B are characteristic diagrams showing a relationship between the average flow velocity within the pipeline and the surface potential variations of the processing liquid supply path 2 at the positions Reg IN and Reg OUT, respectively, when adjusting the flow velocity by using a pump provided at the upstream side of the first valve V1. FIG. 4A depicts data of Reg IN, and FIG. 4B depicts data of Reg OUT. In the drawings, Δ plots data obtained when the regulator 31 is provided, and ◇ plots data obtained when the regulator 31 is not provided. The opening degree of the regulator 31 is fixed. If the regulator 31 is provided, a large pressure loss is involved. If the regulator 31 is not provided, on the other hand, there hardly occurs a pressure loss. As can be seen from these data, in case of Reg IN, it is found out that a minus value of the surface potential variation is increased as the average flow velocity (a pushing force of the pump) is increased, and the surface potential variation is found to be larger when the pressure loss is large. Meanwhile, in case of Reg OUT, it is observed that a plus value of the surface potential variation is increased with the rise of the average flow velocity when the pressure loss is large, whereas a minus value of the surface potential variation is increased with the rise of the average flow velocity when the pressure loss hardly exits.

As can be seen from FIG. 2A to FIG. 4B, in case that the pressure loss is large, by the flowing of the processing liquid, the surface potential is changed to the minus side at the position Reg IN and to the plus side at the position Reg OUT. Regarding the reason for this, when the pressure loss is large, the processing liquid is strongly positively charged whereas the flow path member is strongly negatively charged due to the flowing of the processing liquid having a high liquid pressure and a large pressure variation within the regulator 31. Further, it is deemed that, since the processing liquid is moving to the downstream side, the negatively charged state of the flow path member is highly dominant at the position Reg IN. On the other hand, it is deemed that, though the charge amounts of the processing liquid and the flow path member are small, the positively charged state of the processing liquid becomes highly dominant at the position Reg OUT because the strongly positively charged processing liquid is sent to the measurement point.

As can be clearly seen from the above description, the charge amounts of the processing liquid and the flow path member are varied depending on the degree of the pressure loss within the processing liquid supply path 2, the degree of the flow velocity, etc. When the pressure loss within the processing liquid supply path 2 is large or the flow velocity is high, the charge amounts are increased because the frictional force between the processing liquid and the flow path member is increased. In view of this, according to the exemplary embodiment, the flow path member is grounded at a portion where a large pressure loss occurs. Further, in order to suppress the charge amount of the processing liquid discharged to the wafer W from the nozzle, the sum of the charge amounts of the processing liquid and the flow path member is monitored at a position closest to the nozzle, and the charge amounts are controlled. In general, when monitoring the charge amount, it is sufficient that the charge amount of the processing liquid is monitored. However, since the configuration in which the electrode configured to monitor the charge amount is closely contacted with the flow path member is provided in order to allow the flowing space of the processing liquid to be sealed, as described later, in this exemplary embodiment, the sum of the charge amounts of the processing liquid and the flow path member is monitored.

Now, the devices for reducing, measuring or controlling the charge amount of the processing liquid, which are provided at the processing liquid supply path 2, will be explained again. A first grounding unit 41 and a first measuring unit 51 are provided at the upstream side of the first valve V1 in sequence from the upstream side. Further, a second grounding unit 42 is provided between the first valve V1 and the regulator 31, and a third grounding unit 43 is provided between the regulator 31 and the supply valve V3. Further, each of the first flow path 21, the second flow path 22 and the third flow path 23 is equipped with a second measuring unit 52 between the filter 33 and the flow detection unit 34. Further, between the dispense valve V6 and the nozzle 11 (12, 13), a charge amount control unit 61 and a third measuring unit 53 are provided in sequence from the upstream side. Furthermore, since the first flow path 21, the second flow path 22 and the third flow path 23 have the same supply devices and the same devices for controlling the charge amount, same reference numerals are used to denote the same parts.

Figure 5A:
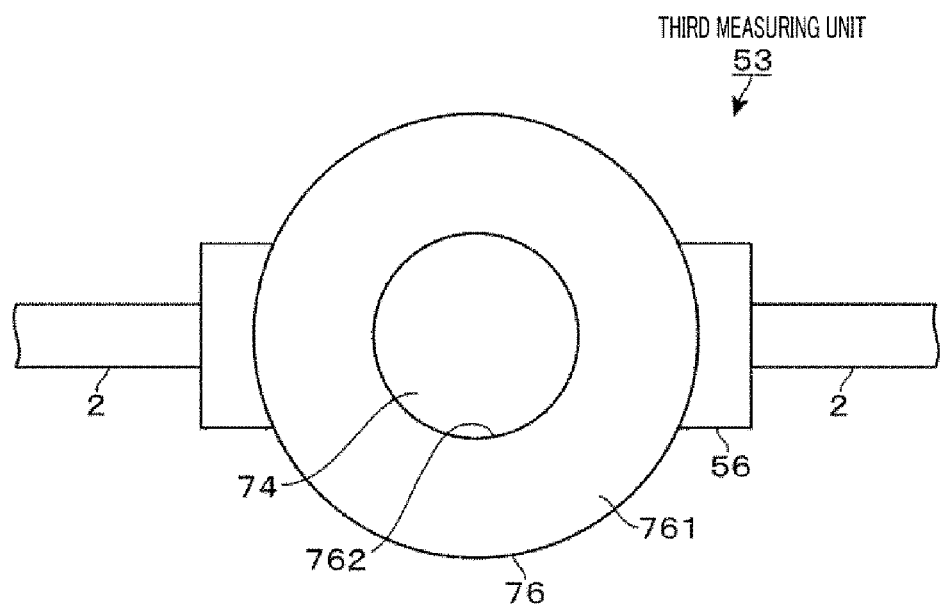
FIG. 5A and FIG. 5B provide a plan view and a longitudinal cross sectional view illustrating an example of a measuring unit provided in the processing liquid supply apparatus, respectively.
Figure 5B:
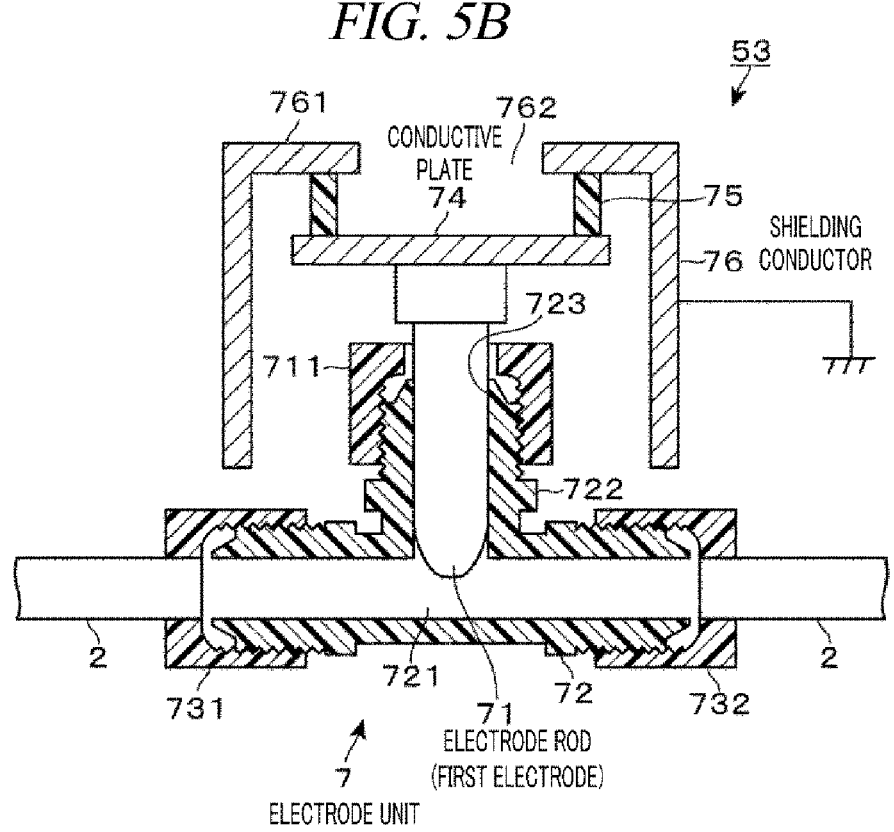
Figure 6:
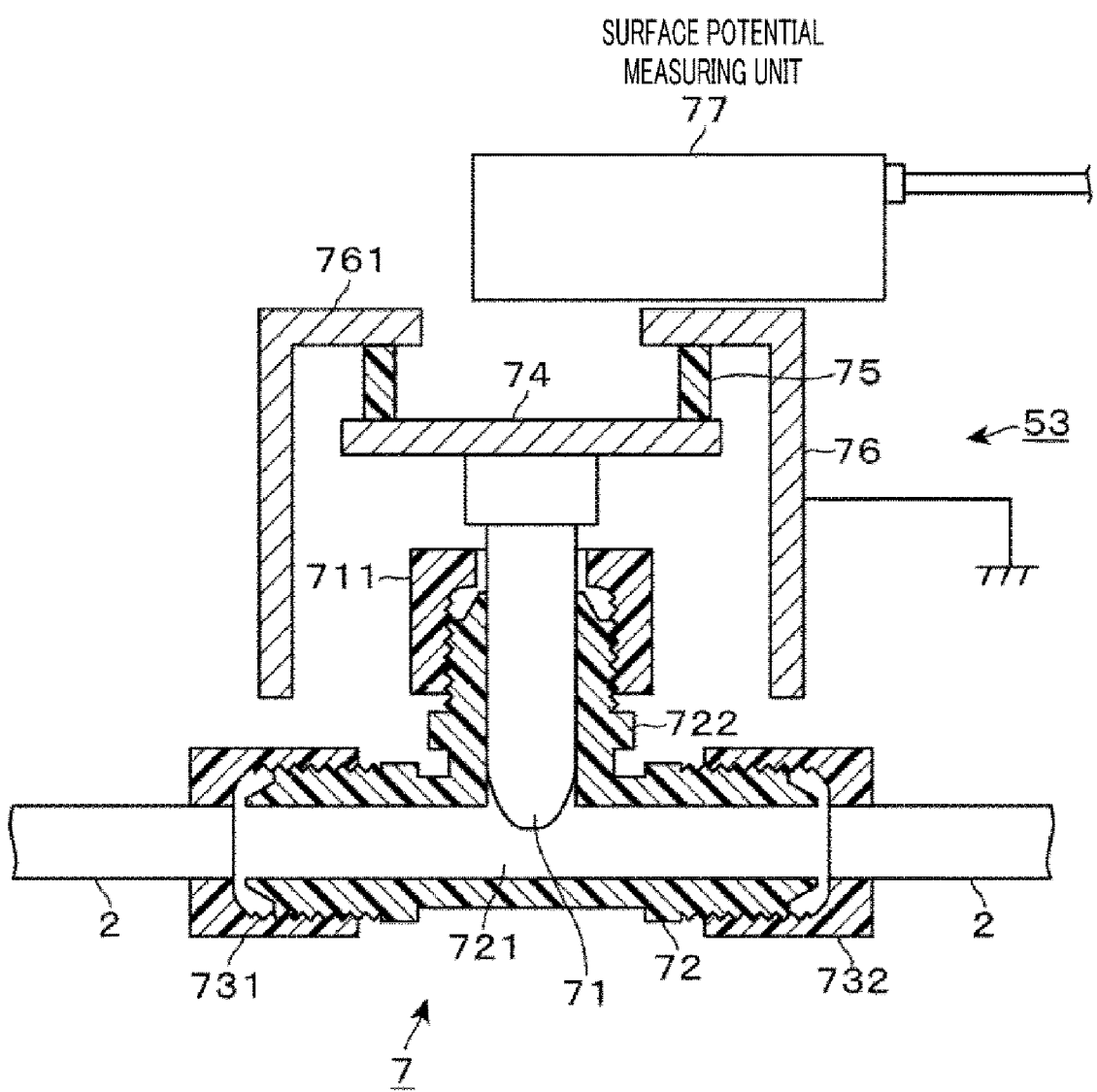
FIG. 6 is a longitudinal cross sectional view illustrating the example measuring unit provided in the processing liquid supply apparatus.

First, the first to third measuring units 51 to 53 will be explained. Since the first to third measuring units 51 to 53 have the same configuration, only the third measuring unit 53 as an example is illustrated in FIG. 5A, FIG. 5B and FIG. 6. Each of the first to third measuring units 51 to 53 is equipped with an electrode unit 7. The electrode unit 7 includes an electrode rod 71 and a liquid contact region forming member 72. The electrode rod 71 of the third measuring unit 53 constitutes a first electrode, and has a rod-shaped body having a circular cross sectional shape, for example. An upper end of the electrode rod 71 is formed to have, for example, a circular plane shape.

A liquid contact portion of this electrode rod 71 is formed by coating a surface of a metal such as, by way of example, stainless steel with a conductive material in order to suppress generation of metal contamination. The conductive material is formed to be a thick film having a thickness of, e.g., 300 μm to suppress the processing liquid from being contacted to the metal region. The conductive material may be, by way of non-limiting example, a fluorine resin having conductivity or static electricity diffusing property (($\leq 10^9 \Omega$)) such as EC series (produced by NIPPON FUSSO CO., LTD), glassy carbon such as AC140S (produced by Nisshinbo Chemical Inc.) or AC140 (produced by Nisshinbo Chemical Inc.), silicon carbide (SiC), or the like.

The liquid contact region forming member 72 is provided at, for example, the processing liquid supply path 2 in a detachable manner, and is configured to hold the electrode rod 71 and form a liquid contact region between the electrode rod 71 and the processing liquid. By way of example, the liquid contact region forming member 72 is made of an insulating material which is the same as the flow path member which forms the processing liquid supply path 2. For example, the liquid contact region forming member 72 is formed along the processing liquid supply path 2, and includes a passageway 721 through which the processing liquid is flown and a holding portion 722 which is formed as one body with the passageway 721 and supports the electrode rod 71. From a substantially central portion of the passageway 721 in a lengthwise direction thereof, the holding portion 722 is extended in a substantially vertical direction with respect to the passageway 721, and an insertion opening 723 for the electrode rod 71 is formed at a leading end of the holding portion 722. For example, the holding portion 722 is formed such that an inner surface thereof is in contact with an outer surface of the electrode rod 71, and a leading end portion of the electrode rod 71 comes into contact with the processing liquid which flows in the passageway 721, when the electrode rod 71 is inserted into the holding portion 722. The electrode rod 71 is connected to the holding portion 722 by, for example, a screw type connecting part 711. With this configuration, the electrode rod 71 is configured to be in contact with the flow path member and the processing liquid of the processing liquid supply path 2.

The liquid contact region forming member 72 is connected to the processing liquid supply path 2 by, for example, screw type connecting parts 731 and 732, and serves as a part of the flow path member. Further, in each of the first flow path 21, the second flow path 22 and the third flow path 23, the electrode rod (first electrode) 71 is arranged at a position in the vicinity of a discharge opening of the nozzle 11 (12, 13), for example, at a position 100 mm to 3000 mm away from the discharge opening along the processing liquid supply path 2. The connecting parts 711, 731 and 732 may be made of, by way of non-limiting example, an insulating fluorine resin which is the same as the material of the processing liquid supply path 2.

Provided on a top surface of the electrode rod 71 of the electrode unit 7 is a conductive plate 74 having, for example, a disk shape, as illustrated in a plan view of FIG. 5A and a longitudinal cross sectional view of FIG. 5B. The conductive plate 74 is configured as a part of the first electrode. For example, a central portion of the conductive plate 74 coincides with a central portion of a horizontal cross section of the electrode rod 71, and a shielding conductor 76 is provided on a top surface of the conductive plate 74 via a supporting body 75 having a cylindrical shape, for example. The supporting body 75 is made of an insulating material such as, but not limited to, PEEK (polyetheretherketone), and the conductive plate 74 and the shielding conductor 76 are made of stainless steel such as, but not limited to, SUS316L.

The shielding conductor 76 is formed to have, for example, a cylindrical shape to cover the vicinity around a lateral side of the electrode rod 71 with a space therebetween. An upper end of the shielding conductor 76 is inwardly curved, and is formed as a ring-shaped top surface portion 761 in which a central portion is opened in a circular shape, for example, when viewed from the top. A rear surface side of the top surface portion 761 is connected to an upper end of the supporting body 75, and an opening 762 at the central portion of the top surface portion 761 is located at an inner position than the supporting body 75. The shielding conductor 76 is grounded to shield an external electric field, and the opening 762 is formed in a concentric shape with the conductive plate 74, for example.

Each of the first to third measuring units 51 to 53 is equipped with a surface potential measuring unit 77 configured to measure a surface potential of the first electrode (electrode rod 71), in this exemplary embodiment, a surface potential of the conductive plate 74, as depicted in FIG. 6. This surface potential measuring unit 77 is provided at the closest position to the top surface portion 761 of the shielding conductor 76, for example, at a position 10 mm upward from the top surface portion 761. Further, a measurement terminal of the surface potential measuring unit 77 is positioned to face the opening surrounded by the shielding conductor 76 (opening formed above the conductive plate 74). As stated before, if the processing liquid is flown in the processing liquid supply path 2, the processing liquid is positively charged and the flow path member is negatively charged, and electric line of force by these electric charges are converged via the first electrode (electrode rod 71), which is connected to the processing liquid and the flow path member, within a region surrounded by the first electrode, the conductive plate 74 and the shielding conductor 76. Since the region surrounded by the conductive plate 74 and the shielding conductor 76 is shielded from the external electric field, an internal potential thereof becomes equal. This potential corresponds to the surface potential of the conductive plate 74 which is a part of the first electrode.

The surface potential measuring unit 77 includes a measurement electrode. This measurement electrode is configured to induce a voltage corresponding to electrostatic capacitance between the measurement electrode and a measurement target object. By oscillating the measurement electrode periodically, an AC-modulated signal is extracted, and the surface potential is measured from this signal. The surface potential measuring unit 77 may be implemented by, for example, a surface potential system such as ZJ-SD produced by Omron Corporation.

By providing the surface potential measuring unit 77 to face the conductive plate 74 as stated above, the charge amounts of the processing liquid and the flow path member are measured as the surface potential of the first electrode (surface potential of the conductive plate 74). As described above, in the present exemplary embodiment, since the electrode rod 71 is closely contacted with the liquid contact region forming member 72 which is a part of the flow path member, the surface potential corresponds to a charged state combining the charged state of the processing liquid and the charged state of the flow path member, and a measurement value of this surface potential is output to a controller 200 to be described later. Further, the shielding conductor 76 may not be provided.

The first measuring unit 51 is provided at the upstream side of the first valve V1 to detect a charged state of the processing liquid which is supplied into the processing liquid supply apparatus from the processing liquid supply source, and the second measuring unit 52 is provided at the downstream side of the filter 33 to detect clogging of the filter 33 or generation of air bubbles. Further, the third measuring unit 53 is provided at the closest position to the nozzle 11 (12, 13) at an upstream side thereof to detect a charged state of the processing liquid which is supplied to the nozzle 11 (12, 13).

Figure 7:
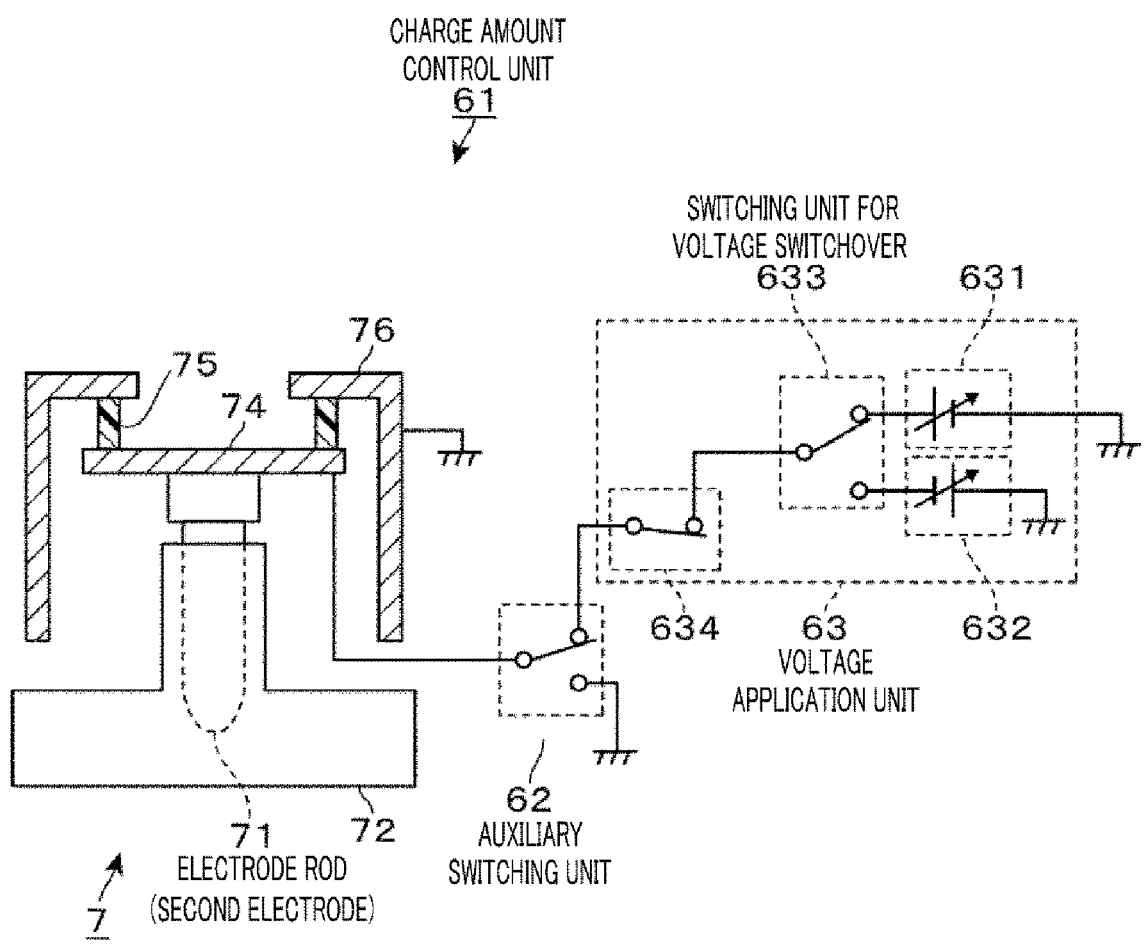
FIG. 7 is a configuration diagram illustrating an example of a charge amount control unit provided in the processing liquid supply apparatus.

Now, an example of the charge amount control unit 61 will be explained with reference to FIG. 7. The charge amount control unit 61 in this example includes, like the first to third measuring units 51 to 53, an electrode unit 7, a conductive plate 74, a supporting body 75 and a shielding conductor 76. An electrode rod 71 of the electrode unit 7 corresponds to a second electrode. For example, in each of the first flow path 21, the second flow path 22 and the third flow path 23, the electrode rod (second electrode) 71 is provided at an upstream position of 10 mm to 5000 mm from the electrode rod (first electrode) 71 of the third measuring unit 53 along the processing liquid supply path 2.

The electrode rod (second electrode) 71 is connected to a voltage application unit 63 via an auxiliary switching unit 62. The auxiliary switching unit 62 is configured to switch a connection point of the electrode rod 71 between the voltage application unit 63 and the ground. Further, the voltage application unit 63 is also configured to control the charge amounts of the processing liquid and the flow path member by applying a voltage to the electrode rod 71 based on the measurement value of the surface potential obtained by the surface potential measuring unit 77 of the third measuring unit 53. In the present exemplary embodiment, the voltage application unit 63 includes, as depicted in FIG. 7, a positive power supply 631 configured to apply a positive voltage, a negative power supply 632 configured to apply a negative voltage, and a switching unit 633 for voltage switchover configured to be connected to either one of the positive power supply 631 and the negative power supply 632 selectively. Further, in the present exemplary embodiment, since the electrode rod 71 serving as the second electrode is closely contacted with the flow path member, it is possible to control the charge amount of the flow path member as well as the charge amount of the processing liquid.

Further, the voltage application unit 63 is further equipped with a switching unit 634 configured to set the electrode rod 71 to be connected to the positive power supply 631 or the negative power supply 632 or disconnected therefrom. Each switching unit may be implemented by, for example, a relay circuit in which two relay switches are arranged in parallel to each other, and one of the two relay switches is turned on while the other is turned off by supplying a power to a relay unit, so that a switch contact point is switched. Furthermore, the charge amount control unit 61 may not be equipped with the shielding conductor 76.

Figure 8:
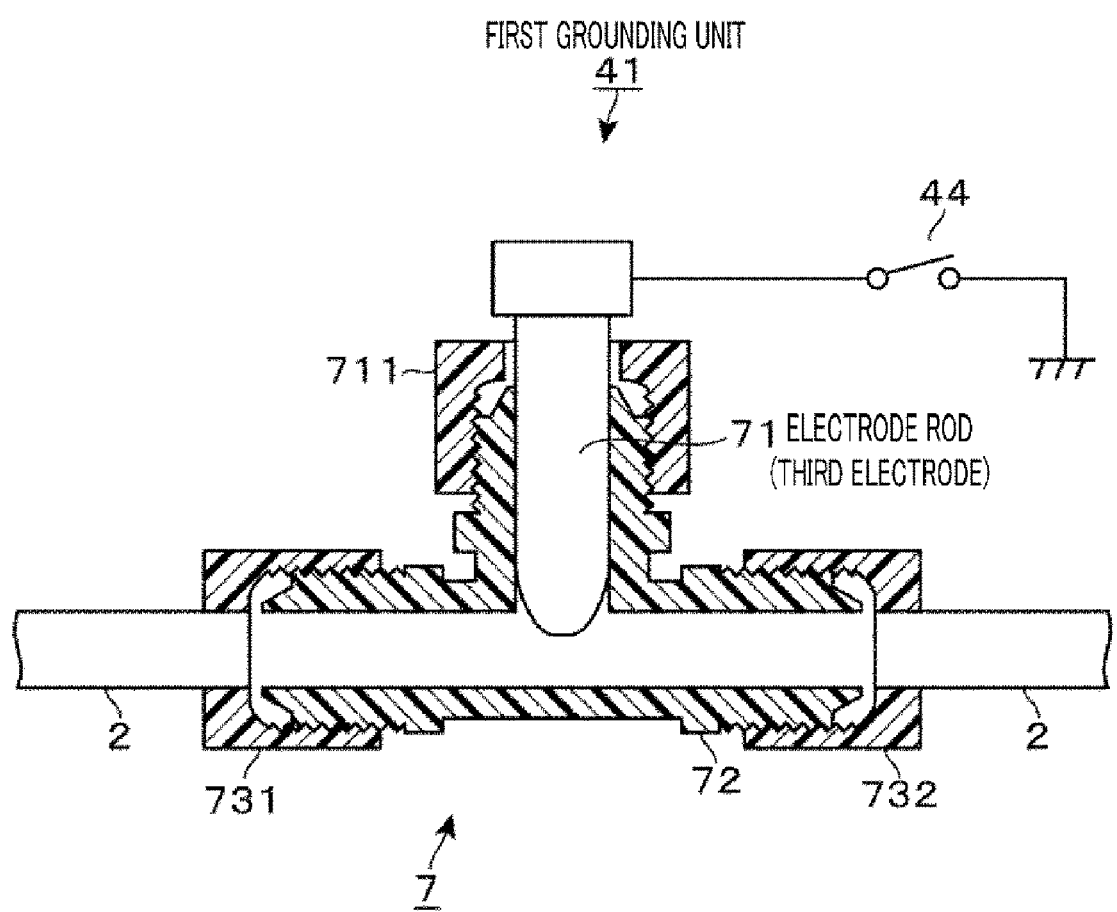
FIG. 8 is a longitudinal cross sectional view illustrating an example of a grounding unit provided in the processing liquid supply apparatus.

Now, the first to third grounding units 41 to 43 will be described. Since the first to third grounding units 41 to 43 have the same configuration, only the first grounding unit 41 as an example is illustrated in FIG. 8. Each of the first to third grounding units 41 to 43 is equipped with an electrode unit 7 having the same configuration as that of the first to third measuring units 51 to 53. An electrode rod 71 of the electrode unit 7 corresponds to a third electrode. By a switching unit 44 for grounding, the electrode rod (third electrode) 71 is switched between a state where it is connected to the ground and a state where it is disconnected from the ground.

Figure 9:
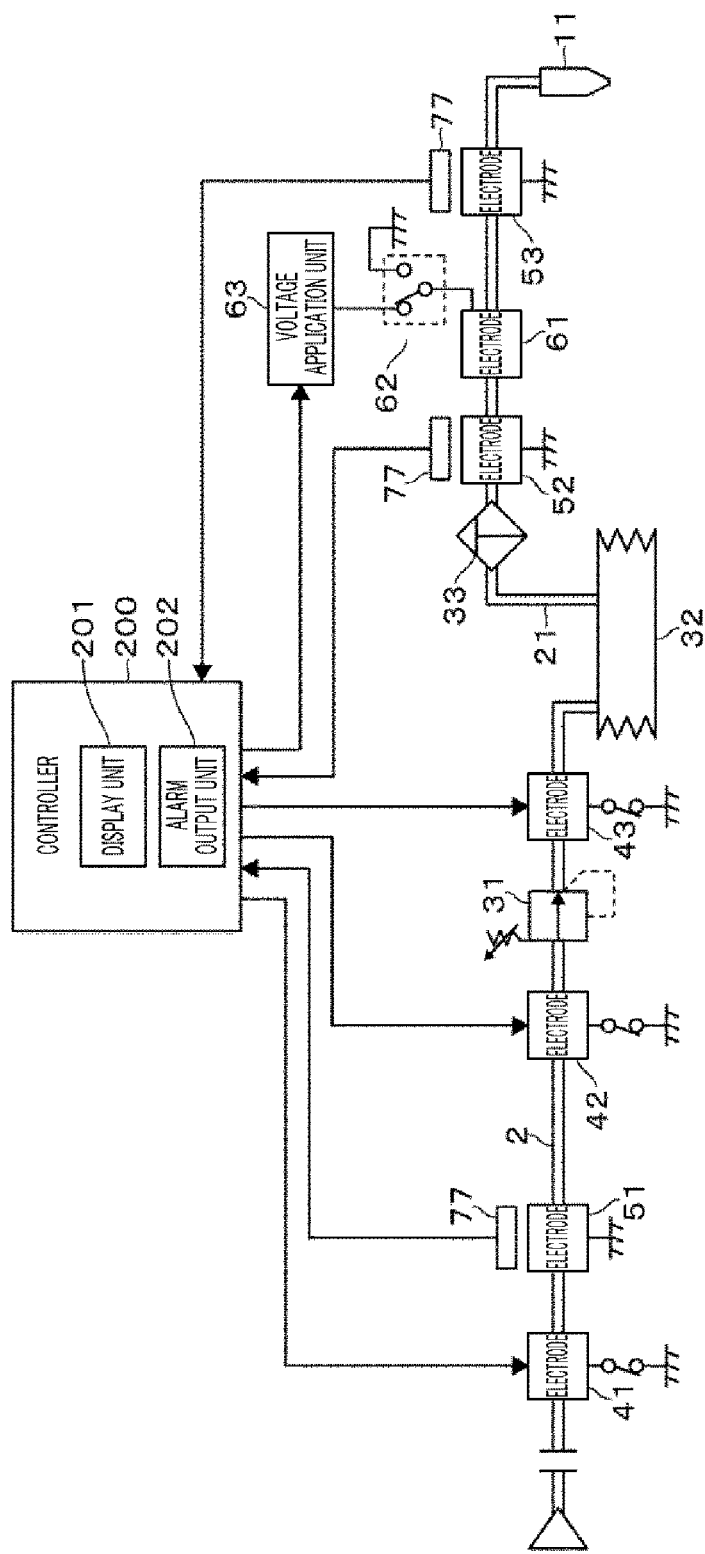
FIG. 9 is a configuration view of a control system of the processing liquid supply apparatus.

As depicted in FIG. 9, the liquid processing apparatus including the processing liquid supply apparatus and the liquid processing modules 100 is equipped with the controller 200 which is implemented by a computer. The controller 200 has a non-illustrated program storage unit. Stored in the program storage unit is a program including commands for controlling the charge amount to be described later and for allowing the liquid processing to be performed in the liquid processing modules 100. The program may be implemented by, but not limited to, software. The controller 200 reads out this program and outputs control signals to individual components of the liquid processing apparatus. As a result, individual operations such as opening/closing of the valves V1 to V7, driving of the pump unit 32, grounding of the electrode rod 71 or voltage application to the electrode rod 71, movement of the nozzles 11 to 13, operating of the substrate holding unit 110, and so forth are controlled, so that the charge amount is controlled and the liquid processing is performed, as will be described later. This program is stored in the program storage unit while being recorded on a recording medium such as a hard disk, a compact disk, a magnetic optical disk or a memory card.

Explanation of the control of the charge amount will be continued. As depicted in FIG. 9, the controller 200 is equipped with a display unit 201 configured to display the surface potentials detected by the surface potential measuring units 77 of the first to third measuring units 51 to 53 at the same time. By way of non-limiting example, the display unit 201 is configured to monitor an analogue output value corresponding to the surface potential. Further, the controller 200 is configured to determine whether the measurement value of the surface potential detected by each of the first to third measuring units 51 to 53 is within an appropriate range, and is configured to output an alarm when the measured surface potential is out of the appropriate range. This alarming operation is performed by an alarm output unit 202 such as an alarm sound generating unit, an alarm lamp, or the like. The appropriate range of the surface potential is set for each of the first to third measuring units 51 to 53 in each process recipe, for example.

Furthermore, the controller 200 is also configured to control the auxiliary switching unit 62, the switching unit 633 for voltage switchover and the switching unit 634 of the charge amount control unit 61 according to a process recipe. To elaborate, by comparing the measurement value of the surface potential obtained by the third measuring unit 53 and a target value, the switching unit 633 for voltage switchover is controlled to be connected to the negative power supply 632 when the measurement value is deviated to the positive side from the target value or connected to the positive power supply 631 when the target value is deviated to the negative side from the target value. Further, the auxiliary switching unit 62 is controlled such that the connection point thereof is switched to the ground when the target value of the surface potential is a zero potential and when the discharge of the processing liquid is stopped (that is, when the processing liquid is not flowing in the processing liquid supply path 2).

Furthermore, when the target value of the surface potential is other than the zero potential, the switching unit 634 is controlled by, by way of non-limiting example, a PWM (pulse width modulation) method or a PID method such that a state in which the switching unit 634 is connected to the positive power supply 631 or the negative power supply 632 and a state in which the switching unit 634 is disconnected therefrom are alternately repeated.

A processing liquid supply process for supplying the processing liquid toward the wafer W from the nozzle includes multiple stages, and the target value of the surface potential is previously set as the recipe according to each of the multiple stages. Further, a cycle in which the electrode rod (second electrode) 71 is intermittently connected to the positive power supply 631 or the negative power supply 632 by the switching unit 634 is previously set for each recipe.

These target values and the cycles are determined through an experiment for achieving optimization, and the cycles are optimized according to the flow velocity of the processing liquid at a time when the processing liquid is discharged. In this way, when the target value of the surface potential is a zero potential, the electrode rod (second electrode) 71 is controlled to be connected to the ground side. When the target value of the surface potential is other than the zero potential, the electrode rod (second electrode) 71 is connected to the voltage application unit 63 periodically, and is controlled, based on the measurement value of the surface potential, to be connected to the positive power supply 631 or the negative power supply 632 according to the target value.

Further, in each of the first to third grounding units 41 to 43, the switching unit 44 for grounding is controlled according to a process recipe such that the electrode rod (third electrode) 71 is grounded when the processing liquid is flowing in a region where the grounding unit 41 (42, 43) is provided, whereas the electrode rod 71 is disconnected from the ground when the processing liquid is not flowing in this region. To the contrary, it is also possible to control the switching unit 44 for grounding such that the electrode rod (third electrode) 71 is disconnected from the ground when the processing liquid is flowing in the region where the grounding unit 41 (42, 43) is provided, whereas the electrode rod 71 is grounded when the processing liquid is not flowing in this region.

Now, an operation according to the exemplary embodiment will be discussed. By opening the first valve V1, the processing liquid is supplied into the processing liquid supply path 2 from the processing liquid supply source at a preset pressure. First, the first valve V1 and the supply valve V3 are opened, and a preset amount of processing liquid is stored within the pump 321 by operating the pump unit 32. Then, air bubbles in the processing liquid within the pump 321 are removed while draining the processing liquid through the drain path 322 by opening the valve V5. Then, after the valve V5 is closed, the discharge valve V4 is opened and the pump unit 32 is operated. The processing liquid is flown through the filter 33, and the processing liquid supply path 2 at the upstream side of, e.g., the dispense valve V6 is filled with the processing liquid.

Subsequently, when discharging the processing liquid from the nozzle 11 (12, 13), the dispense valve V6 is opened for a preset time period while operating the pump unit 32. Accordingly, in each liquid processing module 100, the processing liquid is discharged toward the wafer W from the nozzle 11 (12, 13) for the preset time period, so that the liquid processing is performed. While the processing liquid is being discharged from the nozzle 11 (12, 13), the first valve V1, the supply valve V3 and the discharge valve V4 are still opened, and the processing liquid is supplied into the processing liquid supply path 2 from the processing liquid supply source. When stopping the discharge of the processing liquid from the nozzle 11 (12, 13), the dispense valve V6 is closed.

If the processing liquid is supplied from the processing liquid supply source by opening the first valve V1, the surface potentials measured by the first to third measuring units 51 to 53 are output to the controller 200 and displayed on the display unit 201. Then, it is monitored whether there is abnormality in the surface potentials (charge amounts), for example. If, for example, the surface potential is out of an appropriate range, the alarm output unit 202 outputs an alarm to inform an operator of the abnormality of the charge amount.

By way of example, since the first measuring unit 51 is provided at the upstream side of the first valve V1, an alarm is set forth when the processing liquid having a surface potential exceeding the appropriate range of surface potential is supplied from the processing liquid supply source. Further, since the second measuring unit 52 is provided between the filter 33 and the flow detection unit 34, an alarm is output when the charge amount of the processing liquid is increased over the appropriate range while the processing liquid passes through the regulator 31, the pump unit 32 and the filter 33, for example. Furthermore, since the third measuring unit 53 is provided in the vicinity of the nozzle 11 (12, 13), an alarm is given when the charge amount of the processing liquid discharged to the wafer W exceeds the appropriate range even when the control of the charge amount to be described later is performed.

Now, the control of the charge amount will be explained for an example case where a developing process is performed by supplying a developing solution as the processing liquid to the wafer W. FIG. 10A to FIG. 10C schematically illustrate a liquid processing module 100 configured to perform the developing process. The liquid processing module 100 is equipped with, for example, two kinds of nozzles for supplying the developing solution. One of the two nozzles is a straight tube-shaped nozzle having a discharge opening at a lower side thereof, and the other is a rectangular nozzle having a slit-shaped discharge opening of, e.g., 20 mm. These nozzles are configured to be moved as one body in a radial direction of the wafer W by a common moving device (not shown), for example. For instance, the straight tube-shaped nozzle corresponds to the above-described nozzle 11 (12, 13). Here in the following description, the straight tube-shaped nozzle will be referred to as an auxiliary nozzle 11, and the rectangular nozzle will be referred to as a main nozzle 14 for the convenience of explanation. The developing solution as the processing liquid is supplied into the auxiliary nozzle 11 and the main nozzle 14 from processing liquid supply apparatuses of different systems.

First, while rotating the wafer W, a liquid for pre-wet, e.g., pure water is supplied onto a substantially central portion of the wafer W from a nozzle which is not illustrated in FIG. 10A to FIG. 10C. At this stage, in the processing liquid supply path 2 for each of the auxiliary nozzle 11 and the main nozzle 14, the developing solution is discharged from neither of these nozzles. Thus, in each processing liquid supply path 2, the electrode rods (third electrodes) 71 of each of the first to third grounding units 41 to 43 is set to be disconnected from the ground, whereas the electrode rod (second electrode) 71 of the charge amount control unit 61 is set to be grounded.

Subsequently, as depicted in FIG. 10A, in the processing liquid supply path 2 of the auxiliary nozzle 11, the target value of the surface potential is set to be a minus potential (−E1V), and the developing solution is supplied to the substantially central portion of the wafer W from the auxiliary nozzle 11 while rotating the wafer W at a rotational speed R1. At this stage, since the developing solution is being discharged, the electrode rod (third electrode) 71 is set to be grounded by the switching unit 44 shown in FIG. 8 in each of the first to third grounding units 41 to 43, for example.

Given that the target value of the surface potential is a minus value, the charge amount control unit 61 switches the connection point of the electrode rod (second electrode) 71 to the voltage application unit 63 by the auxiliary switching unit 62, and connects the switching unit 633 for voltage switchover to the negative power supply source 632. Then, while repeating this connected state and the disconnected state periodically by the switching unit 634, the measurement value of the surface potential obtained by the third measuring unit 53 is compared with the target value. If the measurement value is deviated to the negative side from the target value, the switching unit 633 for voltage switchover is switched to the positive power supply 631, whereas if the measurement value is deviated to the positive side, the switching unit 633 for voltage switchover is switched to the negative power supply 632.

In this case, a duty ratio (a ratio of an ON period to the sum of the ON period and an OFF period) in on/off operations of the switching unit 634 is adjusted based on a difference between the measurement value and the target value of the surface potential. For example, if the measurement value is lower than (i.e., an absolute value thereof is larger than) the negative target value of the surface potential, the amount of, e.g., positive charges supplied to the electrode rod 71 is increased by increasing the duty ratio as the difference between the measurement value and the target value of the surface potential is increased. On the other hand, the amount of, e.g., positive charges supplied to the electrode rod 71 is decreased by decreasing the duty ratio as the difference between the measurement value and the target value of the surface potential is decreased. Furthermore, when the measurement value coincides with the target value, a state in which the duty ratio is set to be zero, that is, a state in which the switching unit 634 is turned off is maintained. In this way, a control operation is performed to make the measurement value of the surface potential approach the target value. The target value is, for example, a voltage range having a tolerance range with respect to a target voltage value.

The positive charges or the negative charges may be supplied to the electrode rod 71 by a PID control or the like, instead of the above-described PWM control.

Thereafter, the rotational speed of the wafer W is increased to R2, and there is set a target value (−E2V) of the surface potential according to this rotational speed. Then, the developing solution is supplied to the substantially central portion of the wafer W from the auxiliary nozzle 11. If the rotational speed is increased, a frictional force of the developing solution on the surface of the wafer W is increased, so that the charge amount of the developing solution is changed. Therefore, the target value of the surface potential is set based on the rotational speed. Actually, since the rotational speed is increased stage by stage, the target value of the surface potential is set for each rotational speed.

Then, the discharge of the developing solution from the auxiliary nozzle 11 is stopped, and the auxiliary nozzle 11 and the main nozzle 14 are moved to a peripheral portion side of the wafer W. Then, as shown in FIG. 10B and FIG. 10C, while the wafer W is being rotated, the developing solution is discharged while moving the main nozzle 14 from the peripheral portion toward the central portion of the wafer W in the radial direction, for example. The target value of the surface potential is set to be a plus potential (+E3V) at the peripheral portion side and to be a zero potential (0 V) at the central portion, and the target value of the surface potential is set to be decreased gradually from +E3V to 0 V depending on a position on the wafer W. In this case as well, when the target value is not a zero potential, based on the measurement value of the surface potential, the positive voltage or the negative voltage is applied to the electrode rod (second electrode) 71 according to the target value, as stated above. Further, when the target value is set to be a zero potential, the connection point of the electrode rod (second electrode) 71 is switched to the ground by the auxiliary switching unit 62.

Thereafter, the discharge of the developing solution from the main nozzle 14 is stopped, and the auxiliary nozzle 11 and the main nozzle 14 are retreated to the peripheral portion side of the wafer W. Then, the cleaning is performed by supplying, for example, pure water as a rinse liquid onto the wafer W while rotating the wafer W. Afterwards, the wafer W is dried by supplying a nitrogen gas to the wafer W while rotating the wafer W, and, then, the rotation of the wafer W is stopped. At the above-described individual stages, in the auxiliary nozzle 11 and the main nozzle 14, when the discharge of the processing liquid is stopped, the electrode rod (third electrode) 71 of each of the first to third grounding units 41 to 43 is disconnected from the ground, and the electrode rod (second electrode) 71 of the charge amount control unit 61 is set to be grounded in each processing liquid supply path 2.

In the above-described exemplary embodiment, in supplying the processing liquid to the wafer W through the processing liquid supply path 2 formed by the insulating flow path member, the amount of electric charges corresponding to the sum of the charge amounts of the processing liquid and the flow path member is measured as the surface potential of the conductor. Thus, since the charged states of the flow path member and the processing liquid within the processing liquid supply path 2 can be detected, an appropriate response such as outputting a preset alarm from the alarm output unit 202 can be taken in case that the surface potential is too large or the surface potential is rapidly increased.

Further, by measuring and displaying the surface potential in the state that the processing liquid is being flown in the processing liquid supply path 2, the charged state of the processing liquid, which is changed as the processing liquid is flown, can be detected in a real time. If the fluorine resin forming the processing liquid supply path 2 comes into contact with an organic solvent while a stress is applied thereto, a crack may be easily generated. Meanwhile, a negative type resist tends to be increasingly used, and butyl acetate having high volume resistivity tends to be used as the developing solution. If the volume resistivity is increased, static electricity is rapidly increased due to the friction with the flow path member to be accumulated. For the reason, in the device such as the regulator 31 having a large pressure loss, static electric charges are concentrated in a minute crack portion, so that the fluorine resin is damaged.

Further, a method of circulating the processing liquid without allowing it to stay is mainly performed. Moreover, since the electric charges are accumulated in the processing liquid, there is a concern that the charge amount may be increased. From this view point, it is effective to detect the surface potential of the processing liquid in the processing liquid supply path 2. Further, in case of supplying the processing liquid from the processing liquid supply source to multiple processing liquid supply apparatuses, the first measuring unit 51 is provided at the upstream side of the first valve V1 in each of the processing liquid supply apparatus. Therefore, non-uniformity in the charge amounts of the processing liquid between the processing liquid supply apparatuses can also be detected.

Figure 11A:
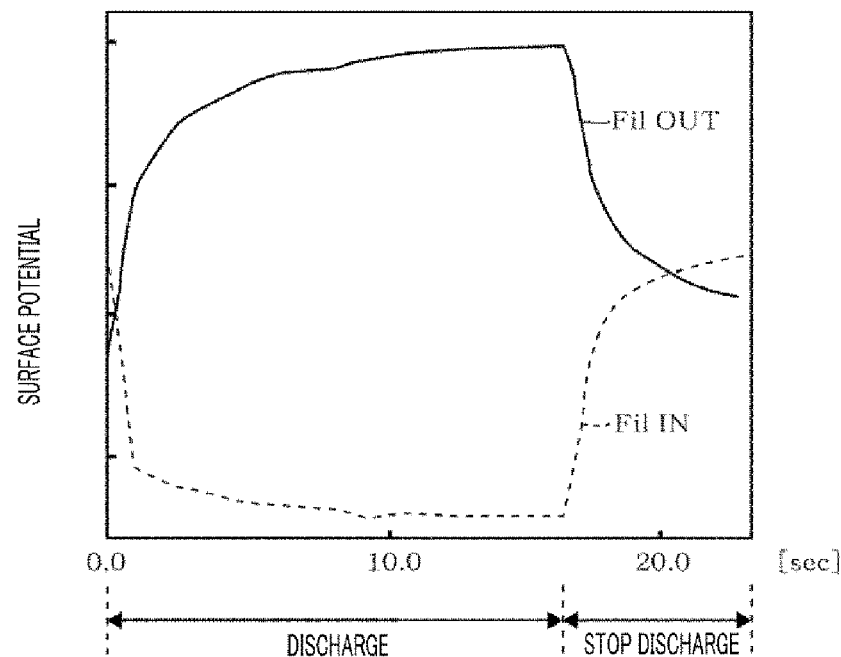
FIG. 11A and FIG. 11B are characteristic diagrams illustrating a relationship between a surface potential and time.
Figure 11B:
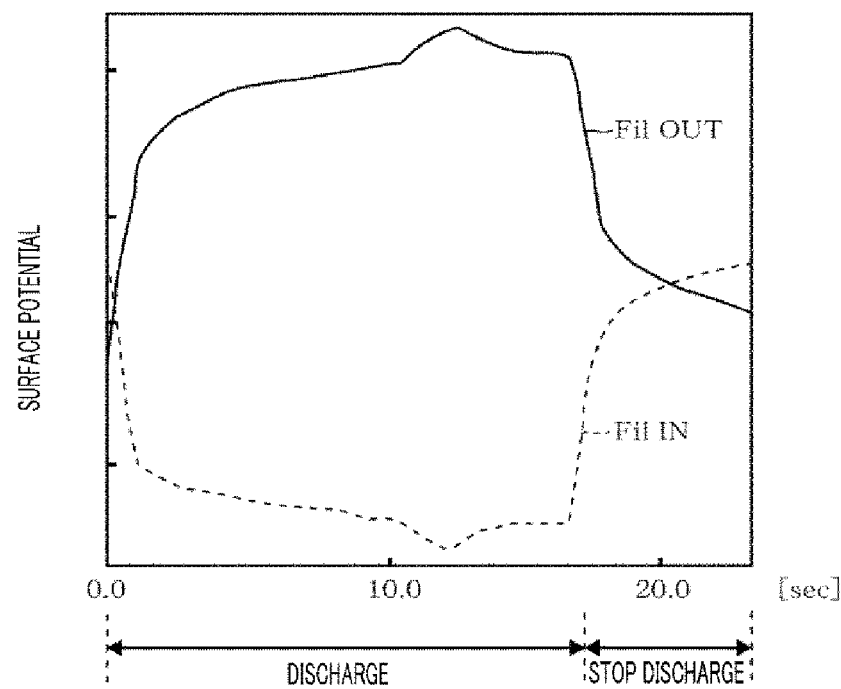

Furthermore, by providing the second measuring unit 52, abnormality such as the clogging of the filter 33 or the mixing of air bubbles can be detected. FIG. 11A and FIG. 11B are characteristic diagrams illustrating a relationship between time and a surface potential at each of a position FilIN closest to the filter 33 at an upstream side thereof and a position FilOUT closest to the filter 33 at a downstream side thereof in the processing liquid supply path 2. FIG. 11A depicts data in the normal state, and FIG. 11B depicts data when there occurs abnormality that several tens of air bubbles are mixed. In the drawings, the data of FilIN is plotted by a dashed line, and the data of FilOUT is plotted by a solid line. As can be seen from these drawings, if the processing liquid starts to be discharged from the nozzle 11 (12, 13), the surface potential changes greatly. At this time, if the air bubbles are mixed in the filter 33, a small peak is generated at the surface potential in each case of FilIN and FilOUT. As stated, by detecting the surface potential in the vicinity of the filter 33, the abnormality of the filter 33 can be detected.

Furthermore, in the present exemplary embodiment, since the voltage is applied to the electrode rod (second electrode) 71 based on the measurement value of the surface potential measured by the third measuring unit 53, it is possible to control the charge amounts of the processing liquid and the flow path member through the electrode rod 71. Thus, even when the charge amount or the flow velocity is too large and thus sufficient charge neutralization may not be achieved just through the grounding, the charge neutralization can be performed securely. Further, it is also possible to suppress occurrence of an accident such as ignition or leakage due to dielectric breakdown of the flow path member, which may be caused by an excessive increase of the charge amount. Moreover, deterioration of accuracy of measurement devices such as the flow detection unit 34 can also be suppressed. In addition, since the positive voltage or the negative voltage is applied to the electrode rod (second electrode) 71 based on the measurement value and the target value of the surface potential, an appropriate control can be easily performed, so that the surface potential can be made to approach the target value rapidly. Further, by providing the auxiliary switching unit 62 or the switching unit 634 in the charge amount control unit 61, the electrode rod (second electrode) 71 can be grounded or connected to the voltage application unit 63 intermittently, so that a highly accurate control can be easily performed according to the target value of the surface potential.

By controlling the charge amount of the processing liquid as stated above, a potential distribution within the surface of the wafer W can be improved when performing the liquid processing. The insulating processing liquid is always positively charged by flow electrification, and a thin film on the wafer W has a potential distribution where a central portion thereof is extremely negatively charged and a potential thereof approaches a zero potential as it goes toward a periphery thereof when the processing liquid is supplied while rotating the wafer W. If the potential distribution within the surface of the wafer W becomes non-uniform, an image may become dim and cannot be measured when measuring a size of a wiring pattern on the wafer W with an inspection device (SEM: Scanning Electron Microscope), for example, or non-uniformity in a device characteristic may occur or a rinse residue may be partially left. Furthermore, if the processing liquid is electrically charged, since an electric current flows through the processing liquid discharged from the nozzle 11 (12, 13), a thin film may be peeled off from the vicinity of a a position where the processing liquid drops, and problems such as dielectric breakdown of a circuit, bending of a discharge path or scattering of a discharged liquid may occur. By controlling the charge amount of the processing liquid, however, the occurrence of these phenomena can be suppressed.

Further, the electrode rod (first electrode) 71 of the third measuring unit 53 and the electrode rod (second electrode) 71 of the charge amount control unit 61 are located at positions within 5000 mm away from the discharge opening of the nozzle 11 (12, 13) without being located at a high pressure loss portion therebetween, the processing liquid having a charge amount close to the target value can be discharged from the nozzle 11 (12, 13). Thus, high process performance can be obtained. Further, even in case of providing the plural nozzles 11 to 13, the charge amounts of the processing liquid discharged from the individual nozzles 11 to 13 can be made same. Moreover, since the surface potential immediately in front of the discharge opening of the nozzle 11 (12, 13) is measured by providing the third measuring unit 53 at the downstream side of the charge amount control unit 61, it is possible to detect the abnormality of the charge amount such as deviation of the surface potential from the appropriate range which may occur even when controlling the charge amount by the charge amount control unit 61.

Moreover, by providing the first to third grounding units 41 to 43 and performing the grounding, a fluid device can be protected even when the charge amount is increased depending on the kind of the processing liquid, the flow condition, or the like in various pressure loss portions of the processing liquid supply apparatus. Additionally, by providing the switching unit 44 for grounding, a control in which the grounding is performed only when the processing liquid is flown in the processing liquid supply path 2 or only when the processing liquid is not flowing in the processing liquid supply path 2 can be performed, so that the charge neutralization can be performed efficiently only when necessary.

Furthermore, the first to third grounding units 41 to 43, the first to third measuring units 51 to 53 and the charge amount control unit 61 are equipped with the common electrode units 7, and the electrode rods 71 forming the electrodes which come into contact with the processing liquid and the flow path member have the same configuration. Since the grounding, the measurement of the surface potential and the control of the charge amount through the voltage application are performed with the electrode rods 71, design for the control of the charge amount and the manufacture thereof are facilitated. Furthermore, since the electrode unit 7 is detachably provided to the flow path member, the grounding unit, the measuring unit and the charge amount control unit can be easily provided at any required places. Further, since the electrode rod 71 is formed by coating the metal with the conductive material, the charge neutralization by the grounding of the processing liquid and the flow path member, the measurement of the surface potential or the control of the charge amount can be performed while suppressing the occurrence of the metal contamination.

In the above description, in the processing liquid supply apparatus, it may be possible to allow the first electrode to be in contact with the processing liquid and the flow path member, measure and display the surface potential and detect the charged states of the processing liquid and the flow path member, for example, when starting the operation of the device, performing maintenance, replacing the processing liquid, and so forth. With this operation, it is possible to detect places where the grounding of the processing liquid and the flow path member or the control of the charge amount through the voltage application is required.

The processing liquid is not limited to the developing solution. By way of non-limiting example, the present inventor has found out that there is a correlation between the charge amount of the rinse liquid during the cleaning process and the number of residues on the wafer W, and the present disclosure is still effective in neutralizing the rinse liquid. An example of the control of the charge amount during the rinsing process will be explained. Pure water as an example of the rinse liquid is also used in a pre-wet process before supplying the developing solution to the wafer W. In this pre-wet process, a target value of the surface potential is set to be a zero potential. Then, in the cleaning process after supplying the developing solution, the target value of the surface potential is set to be –E4V, and the rinse liquid is supplied to a substantially central portion of the wafer W while rotating the wafer W. Then, the rinse liquid and a nitrogen gas for drying are supplied to the wafer W. At this time, the target value of the surface potential is set to a zero potential. In this case as well where the processing liquid is the rinse liquid, the control when the processing liquid is not flowing in the processing liquid supply path 2 (when the processing liquid is not discharged from the nozzles), the control when the processing liquid is flown in the processing liquid supply path 2, the control when the target value of the surface potential is a zero potential, and the control when the target value of the surface potential is not a zero potential are the same as the above-described examples.

In the above description, the configuration of the first to third electrodes is not limited to the exemplary embodiment stated above, and any configuration may be adopted as long as the electrodes come into contact with the processing liquid and any configuration of the surface potential measuring unit may be adopted as long as the surface potential of the conductor configured as the first electrode is measured. Further, the voltage application unit 63 may not necessarily include the switching unit 634, and the second electrode may be connected to the voltage application unit 63 via the auxiliary switching unit 62. In this case, when comparing the measurement value of the surface potential and the target value of the surface potential, or when the measurement value of the surface potential coincides with the target value of the surface potential, the voltage application unit 63 may be disconnected by the auxiliary switching unit 62. Further, the electrode rod 71 serving as the third electrode may be configured to be directly grounded not by the grounding switching unit 44. Furthermore, the display unit configured to display the surface potential may be provided in the vicinity of the first to third measuring units 51 to 53, and at least one of the first electrode, the second electrode and the third electrode needs to be coated with the conductive fluorine resin.

Further, the charge amount control units 61 corresponding to the first measuring unit 51 and the second measuring unit 52, respectively, may be provided. With this configuration, the charge amount may be controlled by applying the voltage to the electrode rod 71 forming each corresponding second electrode based on the measurement value of the surface potential of each of the first measuring unit 51 and the second measuring unit 52. Further, the charge amount control unit 61 may be provided with the surface potential measuring unit 77. In this case, the first electrode also serves as the second electrode, and the charge amount is controlled by measuring the surface potential of the conductor corresponding to the potential of the first electrode and by applying the voltage to the first electrode.

In addition, the above-described processing liquid supply path 2 is equipped with the measuring unit configured to measure the surface potential, the display unit configured to display the surface potential, the grounding unit configured to connect the electrode rod to the ground, and the charge amount control unit configured to control the charge amount by applying the voltage to the electrode rod. The processing liquid supply path 2, however, need not be equipped with all of these components as long as it includes the measuring unit. For example, the processing liquid supply path 2 may only be equipped with the measuring unit, the display unit and the grounding unit, or may only be equipped with the measuring unit, the display unit and the charge amount control unit. Moreover, the installation places and the number of the measuring unit configured to measure the surface potential, the grounding unit and the charting amount control unit may not be limited to the aforementioned examples. Further, the exemplary embodiment is not limited to the coating and developing apparatus but may also be applicable to other liquid processing apparatuses such as a cleaning apparatus, an etching apparatus, a film forming apparatus, a substrate bonding apparatus, an exposure apparatus, an inspection apparatus, and so forth. Furthermore, the semiconductor manufacturing process is not merely limited to a process for forming a semiconductor device on the semiconductor wafer, but may be a process for manufacturing a liquid crystal panel by forming a transistor on a glass substrate.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting. By way of example, the high frequency power supply 42 may be connected to the upper electrode via the matching device 46. Further, the above-described mounting table 14 may also be applicable to, in addition to the capacitively coupled plasma processing apparatus, any of various types of plasma processing apparatuses s, such as an inductively coupled plasma processing apparatus, a plasma processing apparatus using a surface wave such as a microwave for plasma generation, and so forth.

I claim:

1. An operating method of a processing liquid supply apparatus which supplies a processing liquid to a substrate from a processing liquid supply path via a nozzle, the operating method comprising;
    measuring a surface potential of a first electrode which is configured to be inserted into an insulating flow path member and in contact with the processing liquid of the processing liquid supply path, wherein the insulating flow path member is disposed between a processing liquid supply source and the nozzle, and forms the processing liquid supply path; and
    displaying the measured surface potential in the measuring of the surface potential of the first electrode.

2. The operating method of claim 1, further comprising:
    outputting an alarm when the measured surface potential is deviated from a preset range.

3. The operating method of claim 1,
    wherein the processing liquid supply apparatus includes:
    a second electrode configured to be in contact with the processing liquid of the processing liquid supply path; and
    a voltage application unit configured to control a charge amount of the processing liquid by applying a voltage to the second electrode based on a measurement value of the surface potential.

4. A non-transitory recording medium having stored thereon computer-executable instructions that, in response to execution, cause a processing liquid supply apparatus configured to supply a processing liquid to a substrate from a nozzle to perform an operating method of the processing liquid supply apparatus as claimed in claim 1.

* * * * *